United States Patent
King

(10) Patent No.: US 7,160,492 B2
(45) Date of Patent: Jan. 9, 2007

(54) ORTHOPAEDIC DEVICE FOR IMPLANTATION IN THE BODY OF AN ANIMAL AND METHOD FOR MAKING THE SAME

(75) Inventor: Richard King, Warsaw, IN (US)

(73) Assignee: DePuy Products, Inc., Warsaw, IN (US)

(*) Notice: Subject to any disclaimer, the term of this patent is extended or adjusted under 35 U.S.C. 154(b) by 345 days.

(21) Appl. No.: 10/310,394

(22) Filed: Dec. 5, 2002

(65) Prior Publication Data

US 2003/0125513 A1 Jul. 3, 2003

Related U.S. Application Data

(60) Provisional application No. 60/340,807, filed on Dec. 12, 2001.

(51) Int. Cl.
B29C 71/00 (2006.01)

(52) U.S. Cl. .................. 264/101; 264/331.15; 264/344; 528/483; 528/497

(58) Field of Classification Search ............... 528/483, 528/497; 264/101, 331.15, 344; 623/20.14
See application file for complete search history.

(56) References Cited

U.S. PATENT DOCUMENTS

| | | | |
|---|---|---|---|
| 4,655,769 A * | 4/1987 | Zachariades | 623/1.49 |
| 5,414,049 A | 5/1995 | Sun et al. | |
| 5,449,745 A | 9/1995 | Sun et al. | |
| 5,478,906 A | 12/1995 | Howard, Jr. | |
| 5,577,368 A | 11/1996 | Hamilton et al. | |
| 5,607,518 A | 3/1997 | Hoffman et al. | |
| 5,650,485 A | 7/1997 | Sun et al. | |
| 5,728,748 A | 3/1998 | Sun et al. | |
| 5,753,182 A | 5/1998 | Higgins | |
| 5,798,438 A | 8/1998 | Sawan et al. | 528/483 |
| 5,879,400 A | 3/1999 | Merrill et al. | |
| 6,017,975 A | 1/2000 | Saum et al. | |
| 6,071,439 A | 6/2000 | Bawa et al. | 284/1.1 |
| 6,168,626 B1 | 1/2001 | Hyon et al. | |
| 6,228,900 B1 | 5/2001 | Shen et al. | |
| 6,242,507 B1 | 6/2001 | Saum et al. | |
| 6,245,276 B1 | 6/2001 | McNulty et al. | |
| 6,281,264 B1 | 8/2001 | Salovey et al. | |
| 6,316,158 B1 | 11/2001 | Saum et al. | |
| 6,369,192 B1 * | 4/2002 | Dufresne et al. | 528/483 |
| 6,372,814 B1 | 4/2002 | Sun et al. | |
| 6,414,050 B1 * | 7/2002 | Howdle et al. | 523/105 |
| 6,448,315 B1 | 9/2002 | Lidgren et al. | 524/110 |
| 6,451,965 B1 * | 9/2002 | Kanada et al. | 528/480 |
| 6,464,926 B1 | 10/2002 | Merrill et al. | |
| 6,506,213 B1 * | 1/2003 | Mandel et al. | 623/16.11 |
| 2001/0027345 A1 | 10/2001 | Merrill et al. | |
| 2002/0007219 A1 | 1/2002 | Merrill et al. | |
| 2002/0037944 A1 | 3/2002 | Shen et al. | |
| 2002/0107300 A1 | 8/2002 | Saum et al. | |
| 2002/0125614 A1 | 9/2002 | King et al. | |

(Continued)

OTHER PUBLICATIONS

Watkins et al., "Fractionation of High Density Polyethylene in Propane by Isothermal Pressure Profiling and Isobaric Temperature Profiling" *The Journal of Supercritical Fluids*, 4, 24-31, (1991).

(Continued)

Primary Examiner—Mark Eashoo
(74) Attorney, Agent, or Firm—Barnes & Thornburg LLP

(57) ABSTRACT

A method of preparing a orthopaedic implant which includes removing low-molecular-weight compounds from a mass of polymeric material from which the implant is made.

19 Claims, 5 Drawing Sheets

U.S. PATENT DOCUMENTS

2003/0208278 A1* 11/2003 Richard .................. 623/20.14
2004/0084795 A1* 5/2004 Hornsby et al. .............. 264/41

OTHER PUBLICATIONS

Lintas et al., "Distribution of Hydrocarbons in Bovine Tissues", *Lipids*, vol. 14, No. 3, 298-303, (1978).

Richard et al., "Decay of Free Radicals in UHMWPE Using Supercritical Fluids".

G. Filardo, et al., "Carboxylation of a Linear Low Density Polyethylene via Gamma Irradiation in Presence of Carbon Dioxide in Subcritical and Supercritical Conditions," *Radiation Physics and Chemistry*, vol. 44, No. 6 (1994), pp. 597-601.

E. Kiran, et al., "Modeling Polyethylene solutions in Near and Supercritical Fluids Using the Sanchez-Lacombe Model," *The Journal of Supercritical Fluids*, vol. 6 (1993), pp. 193-203.

* cited by examiner

ORTHOPAEDIC DEVICE FOR IMPLANTATION IN THE BODY OF AN ANIMAL AND METHOD FOR MAKING THE SAME

This patent application claims priority to U.S. provisional patent application Ser. No. 60/340,807, filed on Dec. 12, 2001, the disclosure of which is hereby incorporated herein by reference.

FIELD OF THE DISCLOSURE

The present disclosure generally relates a polymeric material for use in the construction of a device to be implanted in the body of an animal and associated methods for making the same. The present disclosure particularly relates to an implantable orthopaedic device constructed from a polymeric material and associated methods for making the same.

BACKGROUND OF THE DISCLOSURE

Various polymeric materials possess desirable characteristics which make them suitable for use in the construction of devices to be implanted in the body of an animal (e.g. a human). For example, many implantable orthopaedic prostheses include at least one component constructed from a polymeric material. In particular, a number of implantable prosthetic bearings include an articulating or bearing surface constructed from a polymeric material on which either a natural bone structure or a prosthetic component articulates. Specific examples of such polymeric bearing surfaces include acetabular bearings, glenoid bearings, tibial bearings, and the like, for use in hip, knee, shoulder, and elbow prostheses. In addition, typical prosthetic bearing designs include an engaging surface constructed from a polymeric material. The engaging surface may also include locking features constructed from a polymeric material. These locking features can be configured as pins, tabs, tapered posts, or the like for locking or otherwise securing the bearing to either another component associated with a prosthetic assembly (e.g., a metal shell or tray) or to the bone itself. Accordingly, in light of the above discussion, it should be appreciated that a number of devices for implantation in the body of an animal are constructed from, or include components constructed from, a polymeric material. Therefore, it is desirable to enhance or improve one or more characteristics of a polymeric material which is used in the construction of a device to be implanted in the body of an animal.

SUMMARY OF THE DISCLOSURE

A device for implanting into a body of an animal, and a method of preparing a polymeric material for implantation into a body of an animal, as for example, an orthopaedic implant, in accordance with the present disclosure comprises one or more of the following features or combinations thereof:

A mass of polymeric material to be implanted into a body of an animal may be subjected to a treatment to remove low-molecular-weight compounds. The treatment to remove low-molecular-weight compounds from the polymeric compound may be performed after the polymeric material has been subjected to a free radical quenching process. For example, the polymeric material may be subjected to a free radical quenching process while positioned in a first chamber. Thereafter, the polymeric material may be removed from the first chamber and placed in a second chamber where low-molecular-weight compounds are removed from the polymeric material. The removal of low-molecular-weight compounds from the polymeric material may include heating the polymeric material while being subjected to a pressure less than 1 atmosphere. Alternatively, the removal of low-molecular-weight compounds from the polymeric material may include extracting the low-molecular-weight compounds with a fluid, such as a liquid or a supercritical fluid. Examples of low-molecular-weight compounds comprise those having a molecular weight less than about 5000, a molecular weight less than about 300, or a carbon number equal to, or less than, 20. The low-molecular-weight compounds may be, for example, hydrocarbons such as aliphatic hydrocarbons. An example of a polymeric material which can be utilized in the methods described herein is crosslinked UHMWPE. The polymeric material may be formed into a bearing configured for use in an orthopaedic implant and sterilized. Removing of the low-molecular-weight compounds may occur prior to, or subsequent to, forming the polymeric material into a bearing configured for use in an orthopaedic implant. The bearing formed from the polymeric material may have a concave bearing surface for engaging a convex articulating surface or a convex articulating surface for engaging a concave bearing surface. A polymeric orthopeadic bearing component containing 0.1% or less aliphatic hydrocarbons which have a molecular weight of 5000 or less may be obtained. For example, a polymeric orthopeadic bearing component which is substantially free of aliphatic hydrocarbons which have a molecular weight of 5000 or less may be obtained.

Additional features of the present disclosure will become apparent to those skilled in the art upon consideration of the following detailed description of preferred embodiments exemplifying the best mode of carrying out the subject matter of the disclosure as presently perceived.

DETAILED DESCRIPTION OF THE DISCLOSURE

While the disclosure is susceptible to various modifications and alternative forms, specific embodiments will herein be described in detail. It should be understood, however, that there is no intent to limit the disclosure to the particular forms described, but on the contrary, the intention is to cover all modifications, equivalents, and alternatives falling within the spirit and scope of the disclosure.

The present disclosure generally relates to a polymeric material for use in the construction of a device to be implanted in the body of an animal (e.g. a human) and associated methods for making the same. The present disclosure particularly relates to implantable polymeric devices such as prosthetic orthopaedic bearings and methods for making the same. Such bearings may be utilized in a number of joint replacement or repair procedures such as surgical procedures associated with the hip, shoulders, knees, ankles, knuckles, or any other joint. For example, such implantable prosthetic bearings may be embodied as a glenoid bearing for implantation into a glenoid of a patient, an acetabular bearing for implantation into an acetabulum of a patient, or a tibial bearing for implantation into a tibia of a patient. A typical prosthetic bearing design includes an articulating or bearing surface on which either a natural bone structure or a prosthetic component articulates. In addition, a typical prosthetic bearing design also includes an engaging surface which may include locking features in the form of mechanisms such as pins, tabs, tapered posts, or the like for locking or otherwise securing the bearing to either another component associated with a prosthetic assembly (e.g., a metal shell or tray) or to the bone itself.

Figure 1:
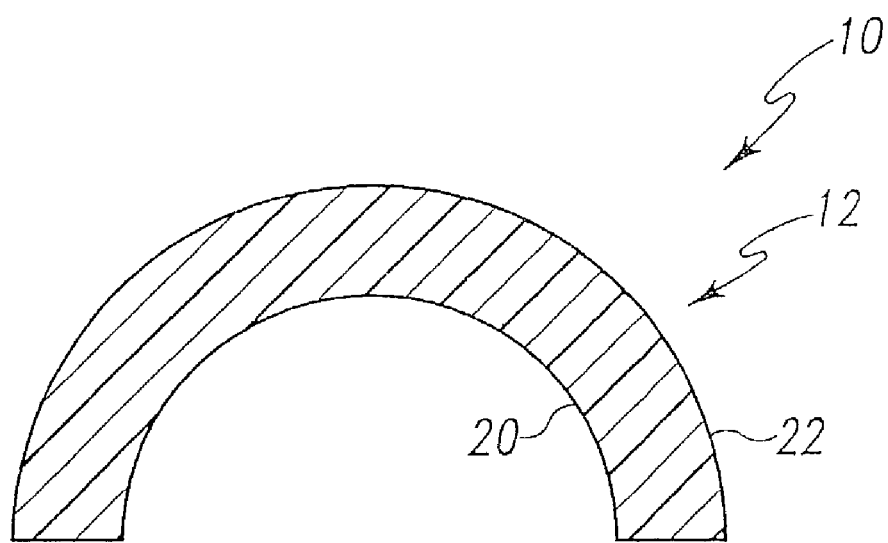
FIG. 1 is a cross sectional view of an implantable prosthetic bearing that may be produced by processes described herein.
Figure 2:
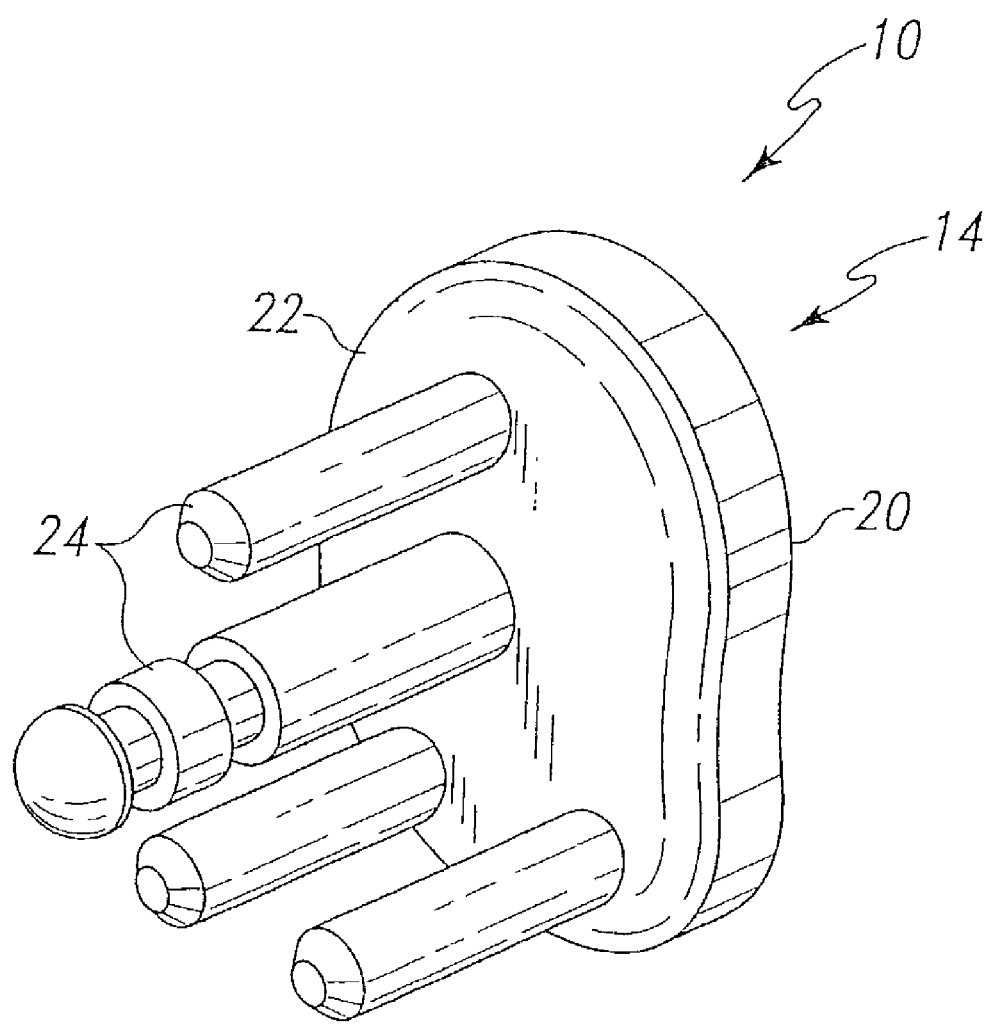
FIG. 2 is a perspective view of an implantable glenoid bearing prosthesis that may be produced by processes described herein.
Figure 3:
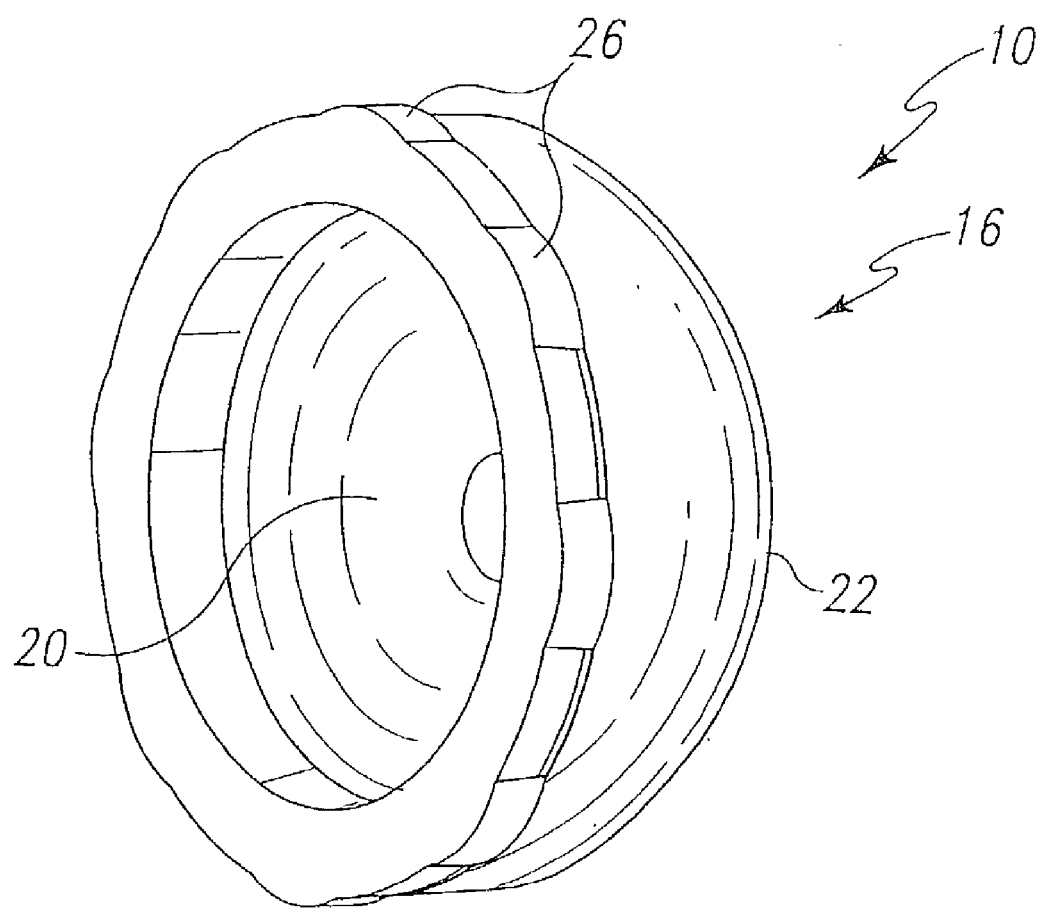
FIG. 3 is a perspective view of an implantable acetabular bearing prosthesis that may be produced by processes described herein.
Figure 4:
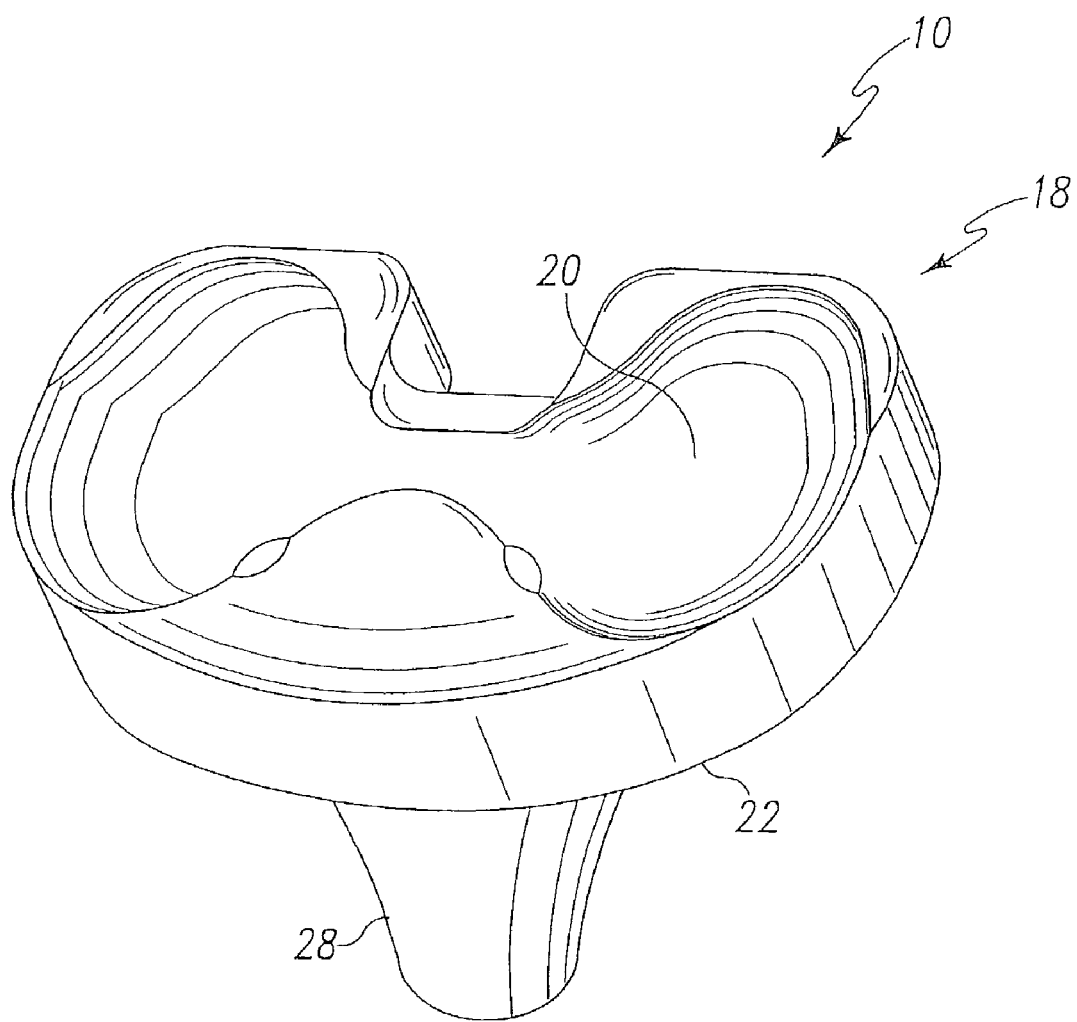
FIG. 4 is a perspective view of an implantable tibial bearing prosthesis that may be produced by processes described herein.

Referring now to FIGS. 1–4, there is shown an implantable polymeric prosthetic bearing 10. The bearing 10 is shown schematically as a bearing 12 in FIG. 1, whereas specific exemplary embodiments of the prosthetic bearing 10, such as a glenoid bearing 14 for implantation into a glenoid of a patient (not shown), an acetabular bearing 16 for implantation into an acetabulum of a patient (not shown), and a tibial bearing 18 for implantation into a tibia of a patient (not shown) are shown in FIGS. 2–4, respectively. Each of the embodiments of the prosthetic bearing 10 includes an articulating or bearing surface 20 on which a natural or prosthetic component bears. For example, in the case of the glenoid bearing 14, a natural or prosthetic humeral head (not shown) bears on the articulating surface 20. Similarly, in the case of an acetabular bearing 16, a natural or prosthetic femoral head (not shown) bears on the articulating surface 20. Moreover, in the case of the tibial bearing 18, a pair of natural or prosthetic femoral condyles (not shown) bear on the articulating surface 20.

Each of the prosthetic bearings 10 also includes an engaging surface 22 which may have a number of features defined therein for engaging either another prosthetic component or the bone into which the bearing 10 is to be implanted. For example, in the case of the glenoid bearing 14, a number of pins or pegs 24 may be defined in the engaging surface 22 thereof. The pegs 24 are received into a number of corresponding holes (not shown) formed in the glenoid surface of the patient. The pins 24 are typically held in place with the use of bone cement. Moreover, if the glenoid bearing 14 is utilized in conjunction with an implanted metal shell, the engaging surface 22 of the bearing 14 may be configured with a tapered post (not shown) or the like for securing the glenoid bearing 14 to the shell.

In the case of the acetabular bearing 16, a number of keying tabs 26 are defined in the engaging surface 22 along the outer annular surface thereof. The keying tabs 26 are received into a number of corresponding keying slots (not shown) defined in an implanted metal acetabular shell (not shown) in order to prevent rotation of the acetabular bearing 16 relative to the implanted shell. In the case of fixation of the acetabular bearing 16 directly to the acetabulum of the patient (i.e., without the use of a metal shell), the engaging surface 22 of the bearing 16 may alternatively be configured with a number of posts or pegs (not shown) which are received into a number of corresponding holes formed in the patient's acetabulum. In such a case, the posts or pegs are typically held in place with the use of bone cement. Moreover, the acetabular bearing 16 may be cemented to the patient's acetabulum without the use of posts or pegs on the engaging surface 22 thereof.

In the case of the tibial bearing 18, a tapered post 28 is defined in the engaging surface 22 thereof. The tapered post 28 is received into a corresponding tapered bore (not shown) defined in an implanted tibial tray (not shown) of a knee prosthesis (not shown). The engaging surface 22 of the tibial bearing 18 may also be configured with features to allow the tibial bearing 18 to be secured directly to the tibia without the use of an implanted tray (e.g., by use of bone cement).

As indicated above, the bearing, or the preform from which it is constructed, may be formed from a polymer. As used herein, the term "polymer" is intended to mean any medical grade polymeric material which may be implanted into an animal (e.g. a human patient), including, but not limited to, polyesters, poly(methylmethacrylate), nylon, polycarbonates, and polyolefins. The term "polymer" is also intended to include both homopolymers and copolymers; thus, "polymer" includes a copolymer comprising ethylene and an acrylate derivative, such as methyl methacrylate, methyl acrylate, ethyl methacrylate, ethyl acrylate, and butyl methacrylate. The term "polymer" also includes oriented materials, such as the materials disclosed in pending U.S. patent application Ser. No. 09/961,842 entitled "Oriented, Cross-Linked UHMWPE Molding for Orthopaedic Applications", which was filed on Sep. 24, 2001, by King et al., which is hereby incorporated by reference, and which is owned by the same assignee as the present application. A specific example of such a polymer is medical grade polyethylene. The term "polyethylene", as defined herein, includes polyethylene, such as a polyethylene homopolymer, high density polyethylene, high molecular weight polyethylene, high density high molecular weight polyethylene, ultrahigh molecular weight polyethylene, or any other type of polyethylene utilized in the construction of a prosthetic implant. A more specific example of such a polymer is medical grade ultrahigh molecular weight polyethylene (UHMWPE).

The starting materials (e.g., polymers such as UHMWPE) for use in the methods described herein may be provided in a number of different forms. For example, the starting materials may be provided as a preform. What is meant herein by the term "preform" is an article that has been consolidated, such as by ram extrusion or compression molding of polymer resin particles, into rods, sheets, blocks, slabs, or the like. The term "preform" also includes a preform "puck" which may be prepared by intermediate machining of a commercially available preform. Polymer preforms such as polyethylene preforms may be provided in a number of different pre-treated or preconditioned variations. For example, as discussed in greater detail below, crosslinked or non-crosslinked (e.g., irradiated or non-irradiated) preforms may be utilized. Such preforms may be quenched or non-quenched.

The starting materials (e.g., polymers and copolymers) may also be provided as powders. What is meant herein by the term "powder" is resin particles sometimes referred to as "flakes". Similarly to as described above in regard to preforms, powders may be provided in a number of different pre-treated or preconditioned variations. For example, crosslinked or non-crosslinked (e.g., irradiated or non-irradiated) powders may be utilized.

The starting materials (e.g., polymers and copolymers) may also be provided as porous structures. What is meant herein by the term "porous structure" is a structure of compacted resin particles. The porous structure may take many forms including blocks or pucks. However, unlike preforms, a porous structure is constructed of unfused or partially fused resin particles. The porous structure may be provided in varying degrees of porosity and may include crosslinked or non-crosslinked (e.g., irradiated or non-irradiated) resin particles. In the case of a porous structure that is crosslinked via irradiation, the resin particles are typically compacted together prior to exposure to gamma or other types of radiation. However, the resin particles may be irradiated prior to compaction, if desired.

In some uses the starting materials (e.g., the preforms, powders, or porous structures) may be "pre-irradiated", "pre-quenched", or otherwise preconditioned prior to use thereof. In particular, it may be desirable for a manufacturer of an orthopaedic implant, such as prosthetic bearings, to purchase material (e.g. polyethylene) which has been irradiated (or otherwise crosslinked), pre-quenched, or otherwise preconditioned by a commercial supplier or other manufacturer of the material. Such "out-sourcing" of pre-conditioning processes is contemplated for use in the processes described herein.

In any case, a starting material in the form of a preform, porous structure, or powder is compression molded, machined, or otherwise shaped or formed into a device for implanting into the body of an animal, for example a bearing, a net-shape bearing, or a near net-shape bearing. What is meant herein by the term "net-shape bearing" is a bearing that is in a shape or condition that is satisfactory for use in a prosthetic implant upon removal of the bearing from a fabrication tool such as a compression molding die without requiring any additional machining. The term "near net-shape bearing", on the other hand, is meant herein to define a bearing which requires a small degree of further manipulation, such as polishing or smoothing, to produce the final bearing. What is meant herein by the term "bearing" is an orthopaedic implant prosthetic bearing of any type, condition, shape, or configuration. As such, the term "bearing", amongst others, includes both net-shape bearings and near net-shape bearings.

As indicated above, the polymer utilized in the construction of a device for implanting in the body of an animal, e.g. implantable orthopaedic device such as a bearing, may be crosslinked by, for example, exposure to radiation such as gamma radiation. Such exposure may be in the exemplary range of 0.5–150 Mrads. However, the concepts described herein may also be utilized in conjunction with non-crosslinked polymeric materials. A specific example of a crosslinked polymeric material that can be utilized in the construction of a device to be implanted in the body of an animal, such as the bearings described herein, is crosslinked UHMWPE. As alluded to above, crosslinked UHMWPE can be obtained by irradiating non-crosslinked UHMWPE with gamma radiation. Examples of commercially available non-crosslinked UHMWPE which can be irradiated to obtain crosslinked UHMWPE include GUR® 1050 (having a molecular weight of about 5 million to about 6 million) and GUR® 1020 (having a molecular weight of about 3 million to about 4 million) both of which are available from Ticona, located in Summit, N.J. An additional example of crosslinked UHMWPE includes, but is not limited to, that disclosed in U.S. Pat. No. 6,316,158 B1 entitled "Process for Medical Implant of Cross-Linked Ultrahigh Molecular Weight Polyethylene Having Improved Balance of Wear Properties and Oxidation Resistance", which was issued on Nov. 13, 2001, to Saum et al. which is incorporated herein by reference.

As indicated above, one manner by which polymers are crosslinked is by gamma irradiation, although other manners such as electron beam or X-ray radiation may also be used. The polymer may be irradiated with gamma radiation at a dose from about 0.5 Mrads to about 150 Mrads, illustratively from about 3 to about 50 Mrads, and illustratively from about 3 to about 15 Mrads using methods known in the art. The irradiation process may be optionally performed under vacuum or in an inert or substantially oxygen-free atmosphere by placing the bearing, preform, porous structure, or powder in a bag. Such a bag may be constructed from materials including, for example, aluminum foil, polyethylene, and the like which are suitable for such irradiation processes. The bag may be optionally evacuated and the atmosphere substantially replaced with an inert gas such as nitrogen, argon, and the like. It will be appreciated, however, that acceptable results may be achieved for certain bearing or material configurations when the irradiation process is carried out under atmospheric conditions, i.e., with some oxygen present. (Note that irradiation of polymers (e.g., UHMWPE) is utilized not only for crosslinking of the material, but also for sterilization purposes. Typically, the irradiation dose used for crosslinking is higher than the irradiation dose used for sterilization.)

In the absence of oxygen, post-irradiation UHMWPE contains not only high-molecular-weight network structures, but also double bonds and, as discussed below in greater detail, low-molecular-weight compounds such as short-chain molecules. While there is no intent to be limited by any particular mechanism, it is believed by persons skilled in the art that irradiation of a polymeric material, such as UHMWPE, initially causes the bonds in the polyethylene chain to be broken by the high energy radiation to form free radicals. Cleavage can occur between carbon and hydrogen atoms in the chain to form a large polyethylene free radical of essentially undiminished molecular weight and a hydrogen free radical. At the other extreme, cleavage can occur between adjacent carbon atoms near the center of the chain resulting in a broken chain with two shorter polyethylene free radicals. Other reactions may occur such as grafting (when a free radical at the end of one chain reacts with a free radical in the center of another chain) or the reacting of a short polyethylene chain with a hydrogen free radical to form lower molecular weight molecules. However, most of these free radicals rapidly recombine with other free radicals in the vicinity to produce crosslinks between chains thereby forming one extremely large molecule of near infinite molecular weight. There is ample evidence for the formation of one extremely large molecule of near infinite molecular weight based on the physical properties of irradiated samples. In particular, the molecular weight of uncrosslinked polyethylene and other polymers is typically determined by measuring the viscosity of a solution in a solvent such as xylene. However, highly crosslinked polyethylene is insoluble even in boiling xylene. As such, a swell test, in which the polymer volume is measured, may be used to determine the molecular weight (or more accurately, the degree of crosslinking) of highly crosslinked polyethylene.

However, not all free radicals rapidly recombine with other free radicals in the vicinity to produce crosslinks between chains. In particular, some free radicals are long lived and may survive for years if not "quenched". Accordingly, it is desirable that a polymeric material, such as UHMWPE, be subjected to a post-irradiation free radical quenching process. What is meant herein by a quenching process are those processes that tend to reduce or substantially eliminate free radical populations in a sample. An example of a known irradiation and quenching regimen utilized to crosslink UHMWPE is briefly set forth below:

- Bars of UHMWPE are identified with a job number and bar number.
- The bars are placed into bags, and placed into a fixture inside of a bagging chamber at room temperature. The atmosphere in the bagging chamber is removed so that the pressure therein is less than 1 atmosphere. Each bag with a bar of UHMWPE therein is subsequently sealed with a heat sealer. Each bag with the UHMWPE bar contained therein is then removed from the bagging chamber after returning the chamber to atmospheric pressure. Each bag is inspected for integrity, and packaged into a labeled box.
- The boxes are shipped to a facility for irradiation.
- Dosimeters for the recording of the level of radiation are placed on the outside of the boxes and the bars are irradiated.
- After irradiation the bars are debagged and placed inside of a vacuum oven to begin a free radical quenching process.
- The bars are heated and soaked at the elevated temperature for a time period under a pressure less than 1 atmosphere.
- The bars are then cooled and soaked at a lower temperature for a time period under a pressure less than 1 atmosphere. The bars are then cooled prior to removal from the chamber and placed on cooling racks. An outer oxidized layer of each bar is also removed after soaking. All temperature ramping operations are conducted in Argon after a backfilling operation.

Accordingly, as contemplated herein, free radical quenching processes include those processes which subject a polymeric material to heat and reduced pressure to quench free radicals. However, it is also contemplated that in some cases quenching can take place under atmospheric pressure, or greater, and in the presence of oxygen. Therefore, as contemplated herein, free radical quenching processes also include those processes which subject a polymeric material to heat under atmospheric pressure, or greater, in the presence or absence of oxygen. In addition, a free radical quenching processes as used herein include those processes which bring a polymeric material in contact with a fluid, such as a supercritical fluid, to quench free radicals.

As alluded to above, irradiation of UHMWPE not only induces crosslinking, but also induces random chain scission. Indeed, it has been reported that the crosslinking to chain scission ratio for polyethylene (post-irradiation) is in the range of about 2.3:1.0 to 3.4:1.0. In particular, as described above, the breakage of a polyethylene backbone can take place close to the end of the chain. In this case, chain scission reactions can generate low-molecular-weight compounds, such as hydrocarbons. In another case, the breakage of polyethylene chain takes place in the middle of the long polyethylene chain. Two such chain breakages occurring near each other on the same molecular chain may also generate low-molecular-weight hydrocarbons.

The low-molecular-weight compounds created by the aforedescribed chain scission conditions may take the form of compounds having, for example, a molecular weight of about 10,000 daltons or less. The low-molecular-weight compounds created by the aforedescribed chain scission conditions may also take the form of compounds having, for example, a molecular weight of about 5000 or less. An additional example, is compounds having a molecular weight of about 300 or less. Moreover, the low-molecular-weight compounds created by the aforedescribed chain scission conditions may also take the form of compounds having, for example, a carbon number of about 40 or less. The low-molecular-weight compounds may also take the form of compounds having, for example, a carbon number of about 30 or less. The low-molecular-weight compounds may also take the form of compounds having, for example, a carbon number of about 20 or less.

The low-molecular-weight compounds created by the aforedescribed chain scission conditions may take the form of low-molecular-weight hydrocarbons such as, for example, aliphatic hydrocarbons. Aliphatic hydrocarbons have the general formula of $C(n)H(2n+2)$, where "n" is an integer. Aliphatic hydrocarbons where "n" is less than or equal to four (4) are gases while those with "n" in the range from five (5) to sixteen (16) are liquid at room temperature. Aliphatic hydrocarbons of octadecane C(18) and eicosane C(20) are liquid at typical body temperatures. Those low-molecular-weight aliphatic hydrocarbons having "n" greater than twenty (20) are often waxy in nature. As used herein, "aliphatic" should be understood to include hydrocarbon species with functional groups, such as one or more double bonds, or one or more carbonyl groups, for example.

Conventional analytical detection techniques such as gas chromatography, including gas chromatography with mass spectroscopy, high performance liquid chromatography, and gel permeation chromatography may be used to detect the presence of low-molecular-weight hydrocarbons or other low-molecular-weight chemical species. However, these analytical detection techniques may have limited capabilities or limited sensitivities. Moreover, the concepts of the present disclosure are not limited in regard to the extraction of any particular upper or lower "n" threshold (i.e., upper or lower molecular weight threshold) of aliphatic hydrocarbons whether or not the presence of such aliphatic hydrocarbons are detectable by conventional techniques.

In any case, since low-molecular-weight hydrocarbons may have a negative impact on mechanical properties, it is desirable to remove them from the implantable device (e.g. a bearing) or from the polymeric material from which the implantable device is constructed. In addition, the extraction of low-molecular-weight compounds enhance the biocompatability of the polymeric material from which the implantable device is constructed. The methods for removing the low-molecular-weight compounds disclosed herein can result in the removal of a substantial amount of low-molecular-weight compounds from a polymeric material. For example, the methods disclosed herein can result in a polymeric material having about 0.2%, or less, by weight of low-molecular-weight compounds, such as low-molecular-weight polyethylenes. The methods disclosed herein can also result in a polymeric material having about 0.1%, or less, by weight of low-molecular-weight compounds. Moreover, the methods disclosed herein can result in a polymeric material being substantially free of low-molecular-weight compounds. The extraction of the low-molecular-weight compounds may take place subsequent to a free radical quenching processes. For example, subsequent to a free radical quenching process that includes subjecting a polymeric material to heat and reduced pressure to quench free radicals, or subsequent to a free radical quenching process that brings a polymeric material in contact with a fluid to quench free radicals.

Extraction (i.e., removal) of these low-molecular-weight hydrocarbons may be achieved in a number of different manners. For example, the low-molecular-weight hydrocarbons may be removed from the bearing or the material from which it is constructed by use of a vacuum evaporation process (i.e., a combination of a medium to high vacuum and the application of heat). For example, vacuum evaporation process can include subjecting the bearing or material from which it is constructed to temperatures in the range from about 155° C. to 270° C. and vacuum pressures in the range from about 0.000001 torr (e.g. with a diffusion pump) to about 100 torr. It should be understood that the temperature may be lowered to, for example, 120° C. if the pressure is very low (i.e., in the presence of a high vacuum). Furthermore, the duration of the vacuum evaporation process can be determined based upon the amount of low-molecular-weight compounds present in the polymeric material, the degree of reduction of the low-molecular-weight compounds present in the polymeric material desired, and the rate at which the low molecular compounds are removed by the vacuum evaporation process under a particular set of conditions for a particular polymeric material. Specific examples of time periods which may be utilized include, but are not limited to, about 2 hours, about 4 hours, or about 8 hours. Other time periods used may be greater (e.g. about 50 hours), or less than, these specific time periods depending upon the above discussed factors.

Alternatively, the low-molecular-weight hydrocarbons may be removed from the bearing or the material from which it is constructed by use of a solvent extraction process (i.e., a combination of a non-polar solvent extraction and subsequent drying process). For example, removal of low-molecular-weight compounds, such as low-molecular-weight polyethylenes, by a solvent extraction/drying process that includes contacting the bearing or the material from which it is constructed with one or more non-polar solvents having a boiling point between about 130° C. and about 250° C. which are capable of inducing swelling in, for example, crosslinked UHMWPE, at an elevated temperature, for example between about 110° C. and about 160° C. It is preferred that the selected non-polar solvent be bioinert, and have a boiling point toward the lower end of the aforementioned boiling point range, i.e. between about 130° C. and about 250° C. Examples of non-polar solvents which may be used in the extraction process include, but are not limited to, octane, decane, and squalene. The duration of extraction can be about 4 hours or longer depending on the radiation dose. A higher radiation dose may require both a higher extraction temperature and a longer extraction duration. As indicated above, after extraction the polymeric material is removed from the non-polar solvent, and any residual solvent remaining in, or on, the polymeric material is removed, for example, by a combination of high vacuum and heat.

One particular solvent extraction process for removing low-molecular-weight hydrocarbons includes contacting the bearing or the material from which it is constructed with o-xylene at a temperature of about 100° C. to about 130° C. for a time period of, for example, about 16 hours. Thereafter, the bearing or material is dried and extracted again with, for example, an ether or an alcohol, to remove any residual o-xylene remaining in, or on, the bearing or material.

Figure 5:
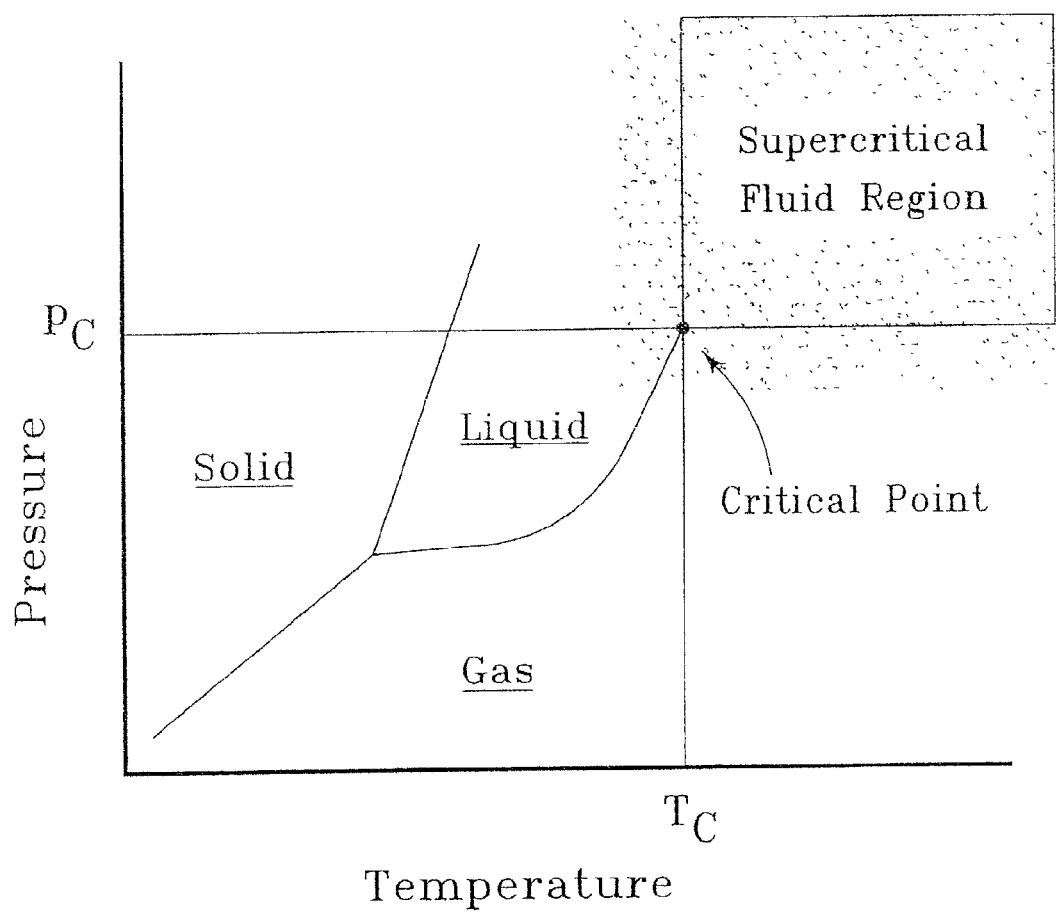
FIG. 5 is a pressure-temperature phase diagram which illustrates the critical point and the associated supercritical fluid region.

The low molecular weight compounds (e.g. hydrocarbons) may be removed from an implantable device (e.g. a bearing) or the material from which it is constructed by use of a supercritical fluid (SCF) extraction process (i.e., a supercritical fluid prepared from, for example, ethers, propane, $CO_2$, and the like). A supercritical fluid is defined herein as a substance where, at a particular temperature, defined as the critical temperature ($T_c$), and at a particular pressure, defined as the critical pressure ($P_c$), the molar volume of the liquid and gaseous phases of the substance are identical. Thus, the distinction between liquid and gaseous phase has been lost and the resulting substance exists as a homogenous "fluid" phase which possesses properties intermediate between the gaseous and the liquid phases. With reference to FIG. 5, the point on the pressure-temperature phase diagram defined by temperature $T_c$ and pressure $P_c$ is the critical point. Above $T_c$, the substance can no longer be condensed at any pressure into a liquid phase. The "supercritical region" is defined herein to include pressure and temperature ranges dictated by the area present on the Temperature-Pressure phase diagram bound by extrapolation above and to the right of the critical point, as shown in the solid-outlined box of FIG. 5. In addition, the gaseous region below the critical pressure extrapolation along with the liquid region to the left of the critical temperature extrapolation may also, under certain conditions, possess supercritical fluid-like characteristics. As a result, these regions, which are commonly utilized to describe "near-critical fluids" and "subcritical fluids", are therefore contemplated for inclusion into the term "supercritical fluid" as used herein. For example, the region of temperatures and pressures designated in the shaded area of FIG. 5 indicates a region which provides the desirable characteristics of a SCF. Some examples of substances that are useful as supercritical fluids are listed in Table I.

The list in Table I is intended to be illustrative only and is not to be interpreted as limiting of the scope or the spirit of substances contemplated to be used in the present disclosure.

TABLE I

Critical points for selected substances useful as supercritical fluids.

| Substance | Critical Temperature ($T_c$, ° C.) | Critical Pressure ($P_c$, psi) |
| --- | --- | --- |
| water | 374 | 3210 |
| ammonia | 133 | 1650 |
| Freon 22 ® | 112 | 598 |
| ethane | 32 | 712 |
| propane | 97 | 624 |
| nitrous oxide | 37 | 1040 |
| carbon dioxide | 31 | 1070 |
| fluoroform | 26 | 711 |
| xenon | 17 | 841 |

An irradiated polymeric material, such as crosslinked UHMWPE, may also be treated with a SCF mixed with other permanent gases, such as hydrogen, nitrogen, and the like, during the low-molecular-weight compound extraction process. The irradiated polymeric material is treated at temperatures and pressures consistent with forming supercritical fluids for such mixtures. The addition of permanent gases or stabilizing gases, such as those described herein, to the SCF may affect the extraction process by having an impact on polymer swelling. In addition, the addition of permanent gases or stabilizing gases to the SCF may affect the extraction process by effectively lowering the critical temperature or critical pressure relative to the temperature and pressure needed to generate the pure SCF. The component of the stabilizing gas, such as hydrogen gas, may be present in from about 0.1% to about 4% by weight, or from about 0.1% to about 1.9% by weight.

Thermal distortion of a bearing constructed from a polymeric material like UHMWPE during SCF treatment likely does not occur at the modest temperatures required for formation of many SCF's. Moreover, given the homogeneous nature of SCF's, deformation of a formed bearing is equally unlikely to occur due to the absence of non-uniform forces exerted by the pressures used in the present invention.

The irradiated polyethylene preferably may be treated with a SCF selected from a group which includes hydrocarbons, fluorocarbons, chlorofluorocarbons, carbon dioxide, nitrous oxide, ammonia, water, and xenon. Preferably, the SCF is selected from a group consisting of hydrocarbons, fluorocarbons, and chlorofluorocarbons. More preferably, the SCF is a hydrocarbon. The polyethylene preform or formed bearing is treated at a temperature near the $T_c$ for the given supercritical fluid, preferably at a temperature of about 50° C. to about 200° C. A polyethylene preform or formed bearing is treated at a pressure near the $P_c$ for the given supercritical fluid, preferably about 500 psi to about 5000 psi for about 4 hours or less, preferably for about 2 hours or less. Illustratively, temperatures below 50° C. or above 200° C. may be desirable for some supercritical fluids in variations of the present process.

An exemplary process includes the irradiation of the preform or formed bearing with a dose of radiation as described above, illustratively from about 1.5 Mrad to about 15 Mrad, followed by treatment with a supercritical hydrocarbon at about 1000 psi to about 3000 psi, optionally containing hydrogen gas, at about 80° C. to about 100° C. for a period of about 2 hours or less. An example of a supercritical fluid which can be utilized in an extraction process described herein is propane at 125° C. and 10,000 psi, with an extraction time of about one hour. The temperature and hold time that is sufficient to, for example, eliminate substantially all of the low molecular compounds in a mass of UHMWPE may be determined by measuring the amount of low-molecular-weight compounds present in the samples using, as discussed in greater detail below, GPC analysis.

Process parameters of such exemplary SCF extraction processes may be controlled so as to allow for the removal of the low-molecular-weight compounds (e.g. hydrocarbons) without degrading or pyrolyzing a polymeric material like UHMWPE. For example, polymeric material to be extracted is placed in a chamber and the chamber is filled with a selected gas, such as carbon dioxide or gaseous hydrocarbons, at a specified pressure and temperature. The gas at this temperature and pressure exists as a supercritical fluid. It solvates, swells the sample of polymeric material and achieves the extraction. Then the supercritical fluid goes through a pressure reduction valve into a collector where the extractables precipitate.

The above described vacuum evaporation process, solvent extraction process, and supercritical fluid (SCF) extraction processes were utilized to remove low-molecular-weight polyethylenes from samples of crosslinked UHMWPE. In particular, samples A, B, C, D, E, F, and G of UHMWPE were crosslinked via gamma irradiation under identical conditions. Sample A was then ground into particles (<1 mm granules) and used as a control for the subsequent GPC analysis. Samples B, C, D, E, F, and G were subjected to an identical quenching process (i.e. melt quenching; note that each sample weighted about 20 grams. After the quenching process sample B was subjected to a reduced pressure of about 0.001 torr for about 1 hour at 140° C. and then ground into particles for subsequent GPC analysis. Sample C was subjected to a reduced pressure of about 0.001 torr for about 2 hours at about 140° C. after the quenching process and then ground into particles for subsequent GPC analysis. Sample D was extracted with decane after quenching. In particular, sample D was placed in contact with decane and maintained within a temperature range of about 110° C. to about 130° C. for a time period of about 4 hours. After extraction with decane, sample D was vacuum dried at about 80° C. for a time period of about 12 hours to remove the decane. Sample D was then ground into particles for subsequent GPC analysis. Sample E was extracted with octanol after quenching. In particular, sample E was placed in contact with octanol and maintained within a temperature range of about 110° C. to about 130° C. for a time period of about 4 hours. Like decane, after extraction with octanol, sample E was vacuum dried at a temperature of about 80° C. for a time period of about 12 to remove the octanol. Sample E was then ground into particles for subsequent GPC analysis. After the quenching process sample F was subjected to a reduced pressure of 0.001 torr for 50 hours at 165° C. and then ground into particles for subsequent GPC analysis. Finally, sample G was extracted with a supercritical fluid after quenching. In particular, sample G was placed in contact with propane at a temperature of about 125° C. under a pressure of about 10,000 psi for about an hour. Sample G was also ground into particles for subsequent GPC analysis.

The ground particles from each sample A, B, C, D, E, F and G were extracted with 1,2,4-trichlorobenzene for about 24 hours at about 135° C. to remove low-molecular-weight compounds (e.g. low-molecular-weight polyethylenes) therefrom. An aliquot of the 1,2,4-trichlorobenzene utilized to extract each sample was then subjected to GPC analysis to determine the amount of low-molecular-weight compounds contained in each sample. GPC analysis was performed using low volume GPC columns packed with styrene/divinylbenzene gel of four different pore sizes. This method of analysis fractionates soluble molecules according to the size of the dissolved species in solution. The mode of detection usually is differential refractometry, UV detection, or RI detection. Other methods of detection can be used including light scattering and fluorescence. The linearity of the detector was measured using stand hydrocarbons and narrow molecular weight polyethylenes. A summary of the GPC conditions and configuration is shown below followed by the GPC analysis results set forth in Table II:

| | | | |
|---|---|---|---|
| Pump: | Waters 150 C | | |
| Detector 1: | dRI @ 128 x | Flow Rate: | 1.00 mL/min |
| Temperature | 135° C. | | |
| Columns: | Waters Styragel HT3 7.8 × 3.00 mm WAT044207 Serial #T 52141 A10 | | |
| | Waters Styragel HT4 7.8 × 3.00 mm WAT044211 Serial #T 12191 101 | | |
| | Waters Styragel HT5 7.8 × 3.00 mm WAT044213 Serial #T 10381 103 | | |
| | Waters Styragel HT6 7.8 × 3.00 mm WAT044215 Serial #T 72800 A01 | | |
| Data: | Millenium 2.10 on NEC computer | Sampling Rate: | 1.0 point per second |
| Eluent: | 1,2,4-Trichlorobenzene | Stabilizer: | Santanox R 0.2% |
| Standards: | 3 N-Alkanes (142–703) +4 Narrow Polyethylenes | | |

-continued

| Curve Fit: | Linear | Correl = | −0.99980 |
|---|---|---|---|
| Sample: | PE | | |
| Sample Prep: | <1 mm × 1 m 135° C. for 24 hours | Sample Conc = | 0.10% |
| Results & Plot: | Triplicate injections | Reference: | None |

TABLE II

| | mg 3.0 mL | Mn | Mw | Mz | Mp | Disp. | Soluble mg/mL | % Soluble | <5000 of % Soluble | <1000 of % Soluble |
|---|---|---|---|---|---|---|---|---|---|---|
| PE 12 k | 7.40 | 11118 | 12662 | 14578 | 11639 | 1.14 | 2.47 | 100% | 0.81% | 0.00% |
| PE 2.1 k | 10.92 | 2068 | 2302 | 2554 | 2234 | 1.11 | 3.64 | 100% | 99.13% | 1.67% |
| PE 283 | — | 246 | 253 | 260 | 258 | 1.03 | — | — | — | — |
| Sample A | 91 | 14973 | 68721 | 119419 | 64973 | 4.59 | 1.70 | 5.60% | 4.71% | 1.41% |
| Sample B | 150 | 7835 | 60460 | 114512 | 55613 | 7.72 | 1.73 | 3.46% | 6.93% | 3.15% |
| Sample C | 154 | 8683 | 62066 | 109258 | 59081 | 7.15 | 2.24 | 4.36% | 5.12% | 2.96% |
| Sample D | 183 | 24121 | 57002 | 102929 | 46367 | 2.36 | 5.15 | 8.45% | 2.61% | 0% |
| Sample E | 215 | 12786 | 51275 | 98552 | 45571 | 4.01 | 2.28 | 3.19% | 6.43% | 1.33% |
| Sample F | 202 | 13153 | 56520 | 124204 | 41430 | 4.30 | 3.68 | 5.46% | 4.65% | 1.34% |
| Sample G | 179 | 25652 | 58113 | 110656 | 47177 | 2.27 | 2.98 | 4.99% | 1.78% | 0% |

The GPC analysis indicated that (i) sample A (the control) contained 0.26% by weight of polyethylenes having a molecular weight of less than 5000 daltons, (ii) sample B contained 0.24% by weight of polyethylenes having a molecular weight of less than 5000 daltons, (iii) sample C contained 0.22% by weight of polyethylenes having a molecular weight of less than 5000 daltons, (iv) sample D contained 0.22% by weight of polyethylenes having a molecular weight of less than 5000 daltons, (v) sample E contained 0.21% by weight of polyethylenes having a molecular weight of less than 5000 daltons, (vi) sample F contained 0.25% by weight of polyethylenes having a molecular weight of less than 5000 daltons, and (vii) sample G contained 0.09% by weight of polyethylenes having a molecular weight of less than 5000 daltons. Accordingly, each sample subjected to a process for removing low-molecular-weight compounds (i.e. samples B, C, D, E, F, and G) contained a reduced amount of polyethylenes having a molecular weight of less than 5000 daltons as compared to control (i.e. sample A).

Thus, based upon the present disclosure, an implantable device fabrication process may be designed to include an extraction process for removing the low-molecular-weight hydrocarbons. For example, a bearing fabrication process may include the following steps: (1) gamma irradiating a preform such as a ram-extruded rod of UHMWPE, (2) quenching the irradiated rod to remove any free radicals present, (3) extracting any present low-molecular-weight hydrocarbons from the quenched rod, (4) annealing the rod (e.g. to increase crystallinity), and (5) machining the rod into the desired shape of an implantable prosthetic bearing.

One or more of the aforedescribed steps may be combined, or even eliminated, based on, for example, the type of extraction process utilized to remove the low-molecular-weight hydrocarbons. For example, if a vacuum evaporation process is utilized, the extraction process may be combined with the quenching process. Specifically, although the vacuum evaporation process may utilize process parameters which exceed the parameters of a conventional quenching process (i.e., elevated temperatures and a medium to high vacuum), the quenching process may be modified so as to be performed at such parameters thereby simultaneously accomplishing both free radical quenching and removal of low-molecular-weight hydrocarbons.

In addition, the extraction process may be performed at any point in the bearing fabrication process subsequent to irradiation. For example, if the fabrication process utilizes a compression molding process in which one or more irradiated preforms, porous structures, or powders are molded into the form of a bearing, low-molecular-weight hydrocarbons may be extracted from the preforms, porous structures, or powders prior to the molding process. Moreover, the molding process itself may be modified such that any low-molecular-weight hydrocarbons present in the irradiated material (or materials) are extracted during the molding process.

Moreover, the extraction process may be performed as one of the final, if not final, fabrication steps. Specifically, the fabrication process may be designed to include a process for removing low-molecular-weight hydrocarbons from net-shape bearings or near net-shape bearings.

The process parameters associated with the extraction process may be varied based on a wide variety of factors such as the type of polymer, the dosage level to which the polymer is exposed, the dimensional makeup of the bearing (in the case of a net shape or near-net shape bearing), the point in the overall fabrication process at which the extraction process is performed, etcetera. The type of extraction process utilized (e.g., vacuum extraction, solvent extraction, or SCF treatment) may also be varied based on similar or different factors.

In short, it is presently contemplated that (1) the extraction process may take the form of any process which is capable of removing low-molecular-weight hydrocarbons from the bearing or from the material from which the bearing is constructed, and (2) such an extraction process may be performed at any point after irradiation in the bearing fabrication process (e.g. after a free radical quenching process). As such, the examples recited herein should not be interpreted as limiting as to the scope of the present disclosure.

The extraction processes described herein may also be useful in the fabrication of non-irradiated bearings. For example, if non-crosslinked polymers, non-irradiated polymers, or polymers which have been crosslinked by manners other than irradiation possess some of low-molecular-weight hydrocarbons, the extraction processes described herein may be utilized to remove such low-molecular-weight hydrocarbons from such polymers (along with bearings constructed therefrom). In essence, the extraction processes described herein may be utilized to remove low-molecular-weight hydrocarbons from polymers irrespective of how such hydrocarbons came to be present in such polymers.

In addition, the extraction processes described herein may be utilized to remove low-molecular-weight chemical species other than hydrocarbons. For example, the extraction processes described herein may be utilized to remove or decompose peroxide or coupling agents from polymers which have been chemically crosslinked.

Similarly, the extraction processes described herein are also useful in the fabrication of bearings which are subjected to radiation for sterilization purposes. While the dosage level utilized in a conventional sterilization process is typically less than the dosage level utilized in a crosslinking process, chain scission may occur nonetheless. As such, the extraction processes described herein may be utilized to remove any present low-molecular-weight hydrocarbons from such sterilized polymers (along with bearings constructed therefrom).

In addition, the extraction processes described herein, along with a number of analytical techniques for determining the amount and type of low-molecular-weight hydrocarbons removed from a given polymer, may be utilize in the formulation of an "optimized" bearing fabrication process for the given polymer. For example, the extraction processes described herein may be utilized to determine an optimal irradiation dosage for a particular polymer at which crosslinking is maximized (or at least enhanced) while the production of low-molecular-weight hydrocarbons is minimized (or at least reduced).

While the invention has been illustrated and described in detail in the foregoing description, such an illustration and description is to be considered as exemplary and not restrictive in character, it being understood that only the illustrative embodiments have been described and that all changes and modifications that come within the spirit of the invention are desired to be protected.

There are a plurality of advantages of the present invention arising from the various features of the prosthetic bearing and methods of making the same described herein. It will be noted that alternative embodiments of each of the prosthetic bearings and methods of making the same of the present invention may not include all of the features described yet benefit from at least some of the advantages of such features. Those of ordinary skill in the art may readily devise their own implementations of prosthetic bearings and methods of making the same that incorporate one or more of the features of the present invention and fall within the spirit and scope of the present invention.

The invention claimed is:

1. A method of preparing a crosslinked UHMWPE bearing for use in an orthopaedic implant, the method comprising:
   subjecting a crosslinked UHMWPE preform, powder or porous structure to vacuum evaporation or solvent extraction to reduce low-molecular-weight compounds present in the crosslinked UHMWPE preform, powder or porous structure to less than 0.2%, by weight; and
   forming the crosslinked UHMWPE preform, powder or porous structure into a bearing configured for use in an orthopaedic implant.

2. The method of claim 1, wherein:
   the removing of low-molecular-weight compounds is performed prior to forming the bearing.

3. The method of claim 1, wherein:
   the removing of low-molecular-weight compounds is performed subsequent to forming the bearing.

4. The method of claim 1, wherein:
   the forming includes forming the crosslinked UHMWPE preform, powder or porous structure into a bearing having a concave bearing surface for engaging a convex articulating surface.

5. The method of claim 1, wherein:
   the forming includes forming the crosslinked UHMWPE preform, powder or porous structure into a bearing having a convex articulating surface for engaging a concave bearing surface.

6. The method of claim 1, wherein:
   the removing includes heating the crosslinked UHMWPE preform, powder or porous structure while subjecting the crosslinked UHMWPE preform, powder or porous structure to a pressure less than 1 atmosphere.

7. The method of claim 6 wherein the crosslinked UHMWPE preform, powder or porous structure is heated at a temperature selected form the range of about 155° C. to about 270° C., and a pressure selected from the range of about 0.000001 torr to about 100 torr.

8. The method of claim 1, wherein:
   the removing includes extracting the low-molecular-weight compounds from the crosslinked UHMWPE preform, powder or porous structure with a fluid.

9. The method of claim 8, wherein:
   extracting the low-molecular-weight compounds from the crosslinked UHMWPE preform, powder or porous structure includes contacting the mass of crosslinked UHMWPE with a liquid.

10. The method of claim 9 wherein the liquid is a non-polar solvent having a boiling point ranging from about 130° C. to about 250° C.

11. The method of claim 8, wherein:
    extracting the low-molecular-weight compounds from the crosslinked UHMWPE preform, powder or porous structure includes contacting the mass of crosslinked UHMWPE with a supercritical fluid.

12. The method of claim 11 wherein the supercritical fluid is a supercritical hydrocarbon administered at a temperature of about 80° C. to about 100° C. and a pressure of about 1,000 to about 3,000 psi.

13. The method of claim 11 wherein the supercritical fluid is propane at 125° C. and 10,000 psi and the crosslinked UHMWPE preform, powder or porous structure is treated for about an hour.

14. The method of claim 1, wherein:
    the low-molecular-weight compounds have a molecular weight of about 5000 or less.

15. The method of claim 1, wherein:

the low-molecular-weight compounds have a molecular weight of about 300 or less.

16. The method of claim 1, wherein:

the low-molecular-weight compounds comprise compounds that have a carbon number of 20 or less.

17. A method of preparing a crosslinked UHMWPE bearing for use in an orthopaedic implant, the method comprising:

subjecting a crosslinked UHMWPE preform, powder or porous structure to vacuum evaporation or solvent extraction to remove an amount of polyethylene molecules having a molecular weight of 5000 or less from the crosslinked UHMWPE preform, powder or porous structure so that the treated crosslinked UHMWPE preform, powder or porous structure contains 0.1% or less of polyethylene molecules having a molecular weight of 5000 or less; and forming the crosslinked UHMWPE preform, powder or porous structure into a bearing configured for use in an orthopaedic implant.

18. The method of claim 17, wherein:

the removing of low-molecular-weight compounds is performed prior to forming the bearing.

19. The method of claim 17, wherein:

the removing of low-molecular-weight compounds is performed subsequent to forming the bearing.

* * * * *